(12) United States Patent
Hoshiko et al.

(10) Patent No.: US 8,753,808 B2
(45) Date of Patent: Jun. 17, 2014

(54) PLATELET AGGREGATION MEASURING METHOD AND PLATELET AGGREGATION MEASURING APPARATUS

(75) Inventors: Susumu Hoshiko, Kobe (JP); Katsushi Kobayashi, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 711 days.

(21) Appl. No.: 12/146,988

(22) Filed: Jun. 26, 2008

(65) Prior Publication Data
US 2009/0004681 A1 Jan. 1, 2009

(30) Foreign Application Priority Data
Jun. 27, 2007 (JP) ................................ 2007-169413

(51) Int. Cl.
*C12Q 1/00* (2006.01)
(52) U.S. Cl.
USPC .............................................................. 435/4
(58) Field of Classification Search
CPC ............................... A61K 38/21; A61K 38/38
USPC .............................................................. 435/4
See application file for complete search history.

(56) References Cited

U.S. PATENT DOCUMENTS

| | | | |
|---|---|---|---|
| 5,325,295 A | 6/1994 | Fratantoni et al. | |
| 5,523,238 A | 6/1996 | Varon et al. | |
| 6,773,923 B2 | 8/2004 | Patzke | |
| 2001/0024803 A1 | 9/2001 | Patzke | |
| 2006/0141629 A1 | 6/2006 | Gitel | |
| 2007/0041874 A1 | 2/2007 | Sukavaneshvar et al. | |
| 2007/0222973 A1 | 9/2007 | Hoshiko et al. | |
| 2008/0044912 A1 | 2/2008 | Yamamoto et al. | |
| 2008/0183431 A1 | 7/2008 | Matsuo et al. | |

FOREIGN PATENT DOCUMENTS

| | | |
|---|---|---|
| EP | 0 458 330 A2 | 11/1991 |
| EP | 1 890 142 A2 | 2/2008 |
| EP | 1 953 547 A2 | 8/2008 |
| JP | 7-146291 A | 6/1995 |
| JP | 2001-281243 A | 10/2001 |
| WO | 02/071037 A2 | 9/2002 |

OTHER PUBLICATIONS

Milner et al. "Ristocetin-mediated interaction of human von Willebrand factor with platelet glycoprotein ib evokes a transient calcium signal: observations with fura-PE3", J Lab Clin Med, 1998, 131:49-62.*
Ermens et al. "Four agglutination assays evaluated for measurement of von Willebrand factor", Clin. Chem. 1995,41(4):510-514.*

* cited by examiner

*Primary Examiner* — Bin Shen
(74) *Attorney, Agent, or Firm* — Sughrue Mion, PLLC

(57) ABSTRACT

A platelet aggregation measuring method comprising: preparing a measurement sample which contains a sample and a reagent which includes a platelet activator; mixing the measurement sample at a first speed; mixing the measurement sample at a second speed which is greater than the first speed after mixing the sample at the first speed; obtaining optical information from the measurement sample while mixing the measurement sample at the second speed; and analyzing aggregation of platelets in the sample based on the optical information is disclosed. A platelet aggregation measuring apparatus is also disclosed.

10 Claims, 13 Drawing Sheets

PLATELET AGGREGATION MEASURING METHOD AND PLATELET AGGREGATION MEASURING APPARATUS

FIELD OF THE INVENTION

The present invention relates to a platelet aggregation measurement method and a platelet aggregation measuring apparatus, and specifically relates to a platelet aggregation measuring method provided with a step of mixing a measurement sample, and a platelet aggregation measuring apparatus provided with a mixing section to mix a measurement sample.

BACKGROUND

Platelet aggregation examination has been known as a test for evaluating platelet function. In a platelet aggregation examination, platelets are caused to aggregate by adding an activator to the platelets to induce the platelets to aggregate, and platelet aggregation is evaluated by monitoring the change in the level aggregation over the course of the platelet aggregation reaction. Platelet aggregation is also known to be promoted by shearing stress on the platelets in the blood stream. Methods which measure platelet aggregation by mixing a measurement sample in order to promote platelet aggregation by adding a shearing stress on the platelets are known (for example, refer to U.S. Pat. No. 6,773,923).

U.S. Pat. No. 6,773,923 discloses a method of measuring platelet aggregation in which a first reaction phase is conducted during which a measurement sample that has been prepared from a sample and reagent is reacted by mixing at a predetermined speed, and thereafter platelet aggregation is measured during a second reaction phase during which the measurement sample is mixed at a speed that is lower than the predetermined speed, or not mixed at all.

The measurement sample is generally prepared by dispensing a sample and a reagent into a predetermined container. The prepared measurement sample is in a state in which the sample and reagent are not uniformly mixed in the measurement sample until the measurement sample is subjected to agitation. Although not clearly stated in U.S. Pat. No. 6,773,923, it is believed that measurement samples are in a state in which the sample and reagent are not uniformly mixed when the measurement sample is subjected to mixing in the first reaction phase in U.S. Pat. No. 6,773,923.

When a reaction (aggregation) is produced by mixing a sample and a reagent of a measurement sample in a state in which the sample and reagent are not uniformly mixed, localized reactions disadvantageously begin between the sample and the reagent when mixing starts. Since the extent of the reaction (aggregation) caused by such localized reactions differs depending on the conditions under which the sample and the reagent are mixed, fluctuations of the measurement results are produced due to the change over time in the aggregation reaction. The problem of unstable measurement results therefore occurs with such measurement methods.

SUMMARY OF THE INVENTION

The scope of the present invention is defined solely by the appended claims, and is not affected to any degree by the statements within this summary.

A first aspect of the present invention is a platelet aggregation measuring method comprising: preparing a measurement sample which contains a sample and a reagent which includes a platelet activator; mixing the measurement sample at a first speed; mixing the measurement sample at a second speed which is greater than the first speed after mixing the sample at the first speed; obtaining optical information from the measurement sample while mixing the measurement sample at the second speed; and analyzing aggregation of platelets in the sample based on the optical information.

A second aspect of the present invention is a platelet aggregation measuring apparatus comprising: a measurement sample preparing section for preparing a sample and a reagent which includes a platelet activator; a mixing section for mixing the measurement sample prepared by the measurement sample preparing section; a control section for controlling the mixing section so as to mix the measurement sample at a first speed, and mix the measurement sample at a second speed that is greater than the first speed after mixing at the first speed; an optical information obtaining section for obtaining optical information from the measurement sample while the mixing section is mixing the measurement sample at the second speed; and an analyzing section for analyzing aggregation of platelets in the sample based on the optical information.

A third aspect of the present invention is a platelet aggregation measuring apparatus comprising: a first dispensing section for dispensing a sample; a second dispensing section for dispensing a platelet activator; a mixing section for mixing the measurement sample that contains a sample dispensed by the first dispensing section and a reagent dispensed by the second dispensing section; a control section for controlling the mixing section so as to mix the measurement sample at a first speed, and mix the measurement sample at a second speed that is greater than the first speed after mixing at the first speed; an optical information obtaining section for obtaining optical information from the measurement sample while the mixing section is mixing the measurement sample at the second speed; and an analyzing section for analyzing aggregation of platelets in the sample based on the optical information.

DETAILED DESCRIPTION OF THE PREFERRED EMBODIMENTS

The preferred embodiments of the present invention will be described hereinafter with reference to the drawings.

The general structure of a blood analyzer 1 of an embodiment of the present invention is described below with reference to FIGS. 1 through 8.

The blood analyzer 1 of the present embodiment optically measures and analyzes the amount and degree of activity of specific substances relating to blood coagulation and fibrinolytic function, and uses blood plasma as a blood sample. The blood analyzer 1 of the present embodiment measures the blood sample coagulation time by optically measuring the blood sample using a coagulation time method, synthetic substrate method, immunoturbidity method, and platelet aggregation method.

Figure 1:
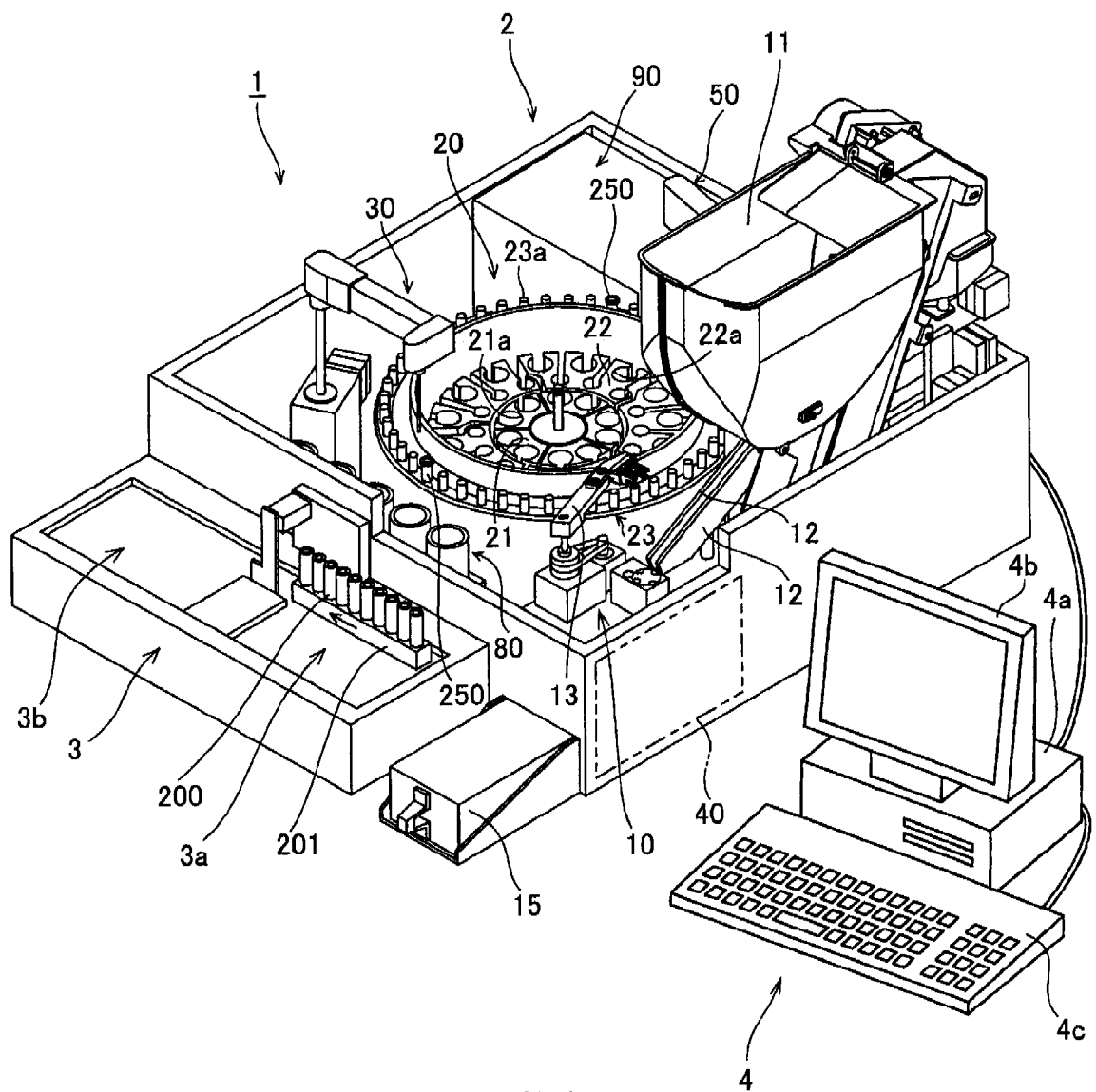
FIG. 1 is a perspective view showing the general structure of an embodiment of the blood analyzer of the present invention.
Figure 2:
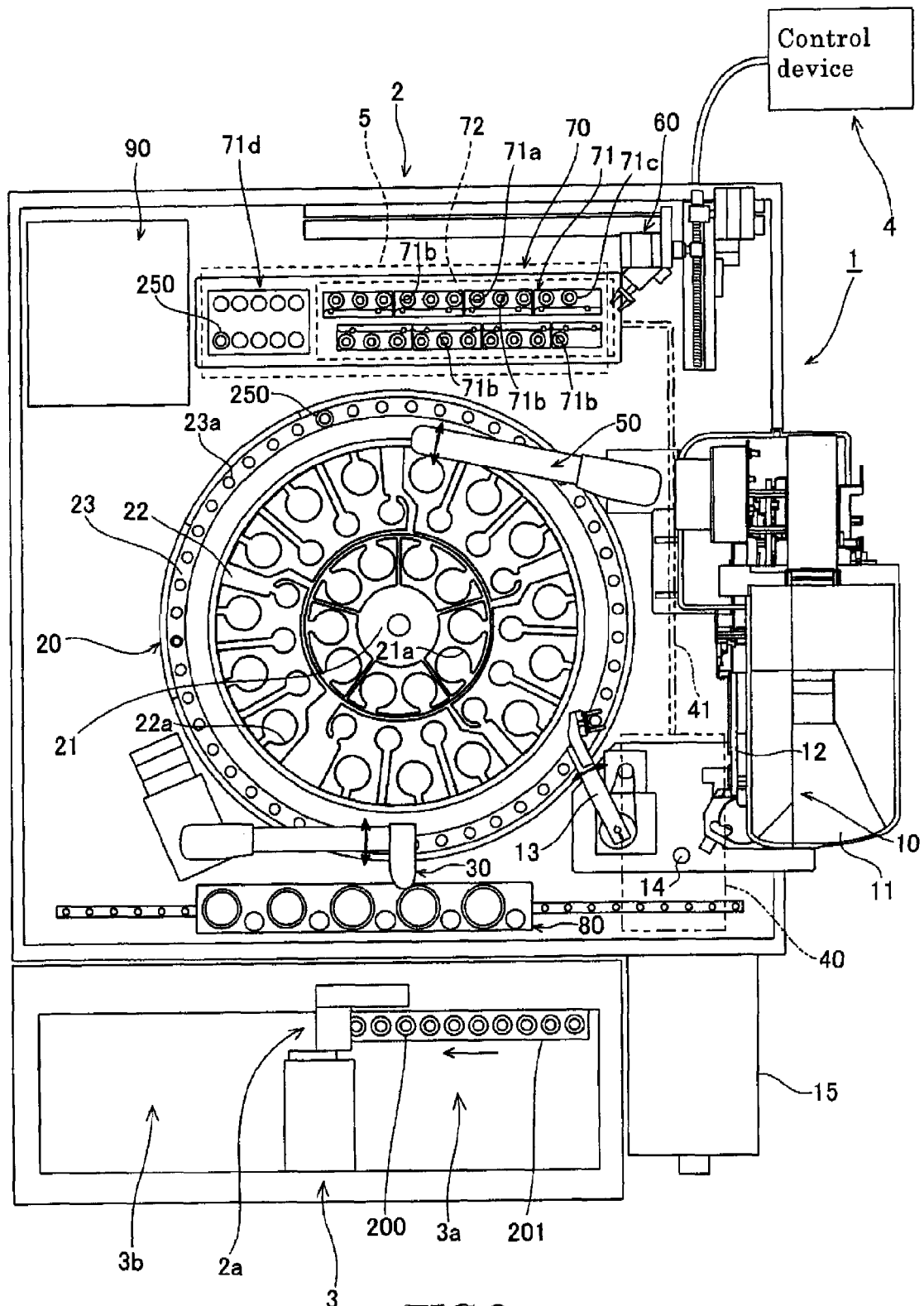
FIG. 2 is a top view corresponding to FIG. 1.
Figure 3:
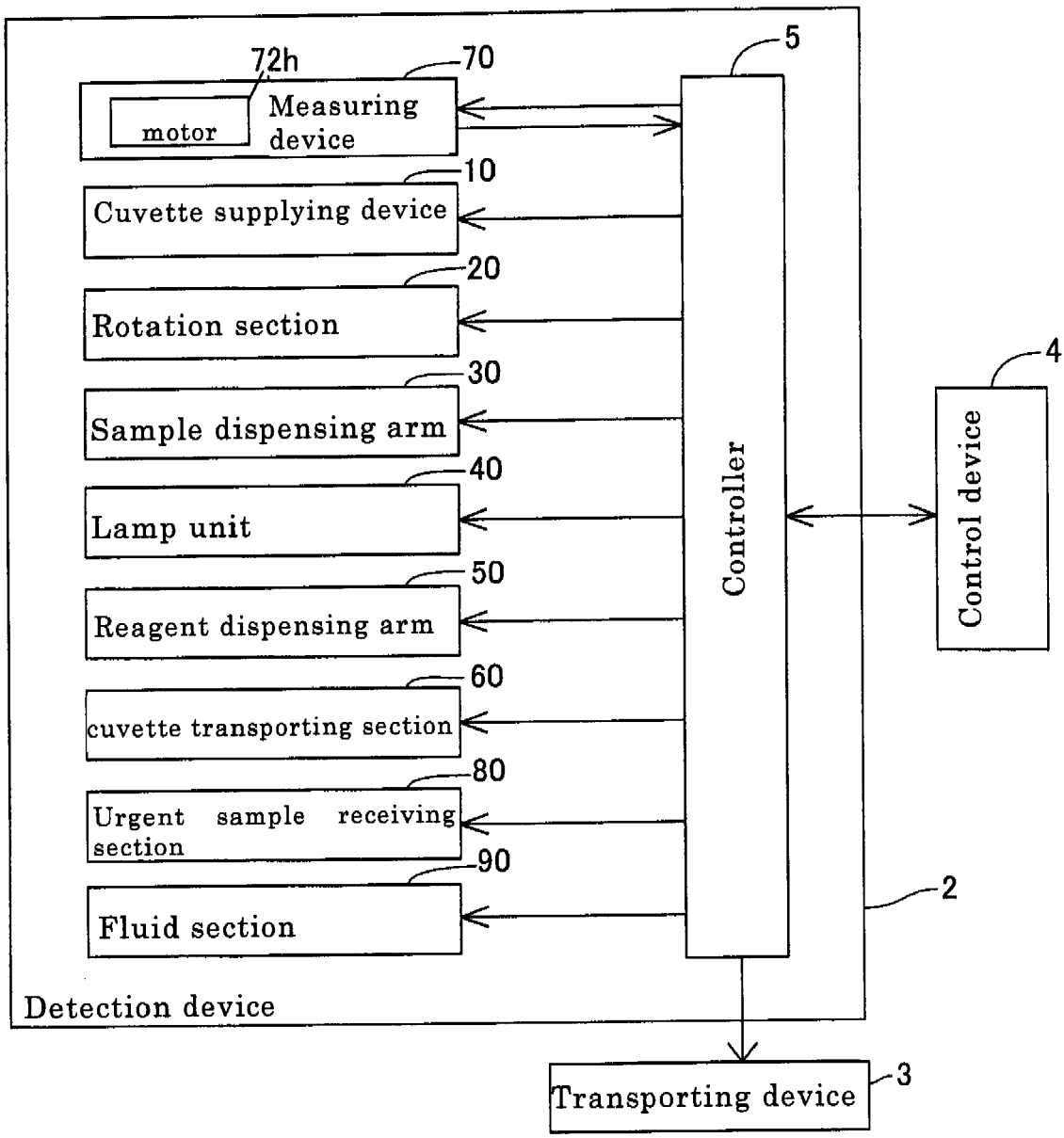
FIG. 3 is a block diagram showing the overall structure of the blood analyzer of FIG. 1.

The blood analyzer 1 is configured by a detection device 2, a transporting device 3 which is arranged on the front side of the detection device 2, and a control device 4 which is electrically connected to the detection device 2, as shown in FIGS. 1 through 3. The detection device 2 and the transporting device 3 are controlled by a controller 5 which is provided within the detection device 2 (refer to FIG. 2).

The transporting device 3 has the function of transporting a rack 201 holding a plurality of test tubes 200 (ten tubes in the present embodiment) that contain blood samples to an aspiration position 2a (refer to FIG. 2) of the detection device 2 so as to supply the blood samples to the detection device 2. The transporting device 3 has a rack receiving region 3a where the racks 201 are placed which hold test tubes 200 that contain unprocessed blood samples, and a rack storage region 3b where the racks 201 are stored which hold test tubes 201 that contain processed blood samples.

The detection device 2 is configured so as to be capable of obtaining optical information relating to a supplied blood sample by optically measuring a blood sample supplied from the transporting device 3. In the present embodiment, optical measurements are performed on blood samples which have been dispensed from a test tube 200 held in the rack 201 of the transporting device 3 into a cuvette 250 (refer to FIG. 1) of the detection device 2. As shown in FIGS. 1 through 3, the detection device 2 is provided with a cuvette supplying device 10, a rotation device 20, a sample dispensing arm 30, a lamp unit 40, a reagent dispensing arm 50, a cuvette transporting section 60, a measuring section 70, an urgent sample receiving section 80, and a fluid section 90.

The cuvette supplying device 10 is configured so as to be capable of sequentially supplying a plurality of cuvettes 250, which have been randomly loaded in the device by a user, to the rotation device 20 when performing measurements using the coagulation time method, synthetic substrate method, or immunoturbidity method. As shown in FIGS. 1 and 2, the cuvette supplying device 10 includes hopper 11 into which a user loads the cuvettes 250, and a catcher 13 which receives the cuvettes that drop from the hopper 11 via guide plates 12 and supplies the cuvettes 250 to the rotation device 20.

As shown in FIG. 2, the detection device 2 is provided with a disposal hole 14 which is used to discard the cuvette 250 and which is disposed at a predetermined distance from the catcher 13, and a disposal box 15 which is arranged below the disposal hole 14. The catcher 13 can remove the cuvette 250 from a cuvette transporting table 23 of the rotation device 20 and discard the cuvette 250 through the disposal hole 14 into the disposal box 15. That is, the catcher 13 is used to both supply and discard the cuvettes 250.

The rotation device 20 is provided to transport, in a rotary direction, the cuvettes 250, which are received from the cuvette supplying device 10, and the reagent containers (not shown in the drawing, which contained reagent used cause coagulation of the blood sample. As shown in FIG. 2, the rotation device 20 is configured by a circular reagent table 21, an annular shaped reagent table 22 which is disposed on the outer side of the circular reagent table 21, and an annular shaped cuvette transporting table 23 which is disposed on the outer side of the annular reagent table 22. The cuvette transporting table 23, and the reagent tables 21 and 22 are rotatable in both clockwise and counterclockwise directions, and the tables are mutually and independently rotatable.

As shown in FIG. 2, the reagent tables 21 and 22 respectively include a plurality of holes 21a and 22a which are provided at predetermined spacing along the circumferential direction. The holes 21a and 22a of the reagent tables 21 and 22 are provided to load a plurality of reagent containers (not shown in the drawings) that hold reagent for coagulating the blood specimen. The cuvette transporting table 23 includes a plurality of cylindrical holders 23a which are provided at predetermined spacing along the circumferential direction. The holder 23a is provided to hold a cuvette 250 which has been supplied from the cuvette supplying device 10. In the case of measurements by the platelet aggregation method in the present embodiment, a cuvette 251 which internally accommodates a mixing element 300 (refer to FIG. 6) can be manually placed by a user into the holder 23a of the cuvette transporting table 23. In the present embodiment the cuvette 251 is approximately cylindrical in shape and measures 6 mm in internal diameter and 29.8 mm in height, and the mixing element 300 is a round rod measuring 1.2 mm in diameter.

The sample dispensing arm 30 dispenses a blood sample, which is contained in a test tube 200 accommodated in a rack 201 loaded in the transporting device 3, into the cuvettes 250 and 251 which are held by the holder 23a of the cuvette transporting table 23.

The sample dispensing arm 30 has the function of aspirating a blood sample contained in a test tube 200 which has been transported to the aspirating position 2a by the transporting device 3, and dispensing the aspirated blood sample into a cuvette 250 which has been transported on the rotation device 20, or into a cuvette 251 which accommodates a mixing element 300 and is placed in the rotation device 20.

Figure 4:
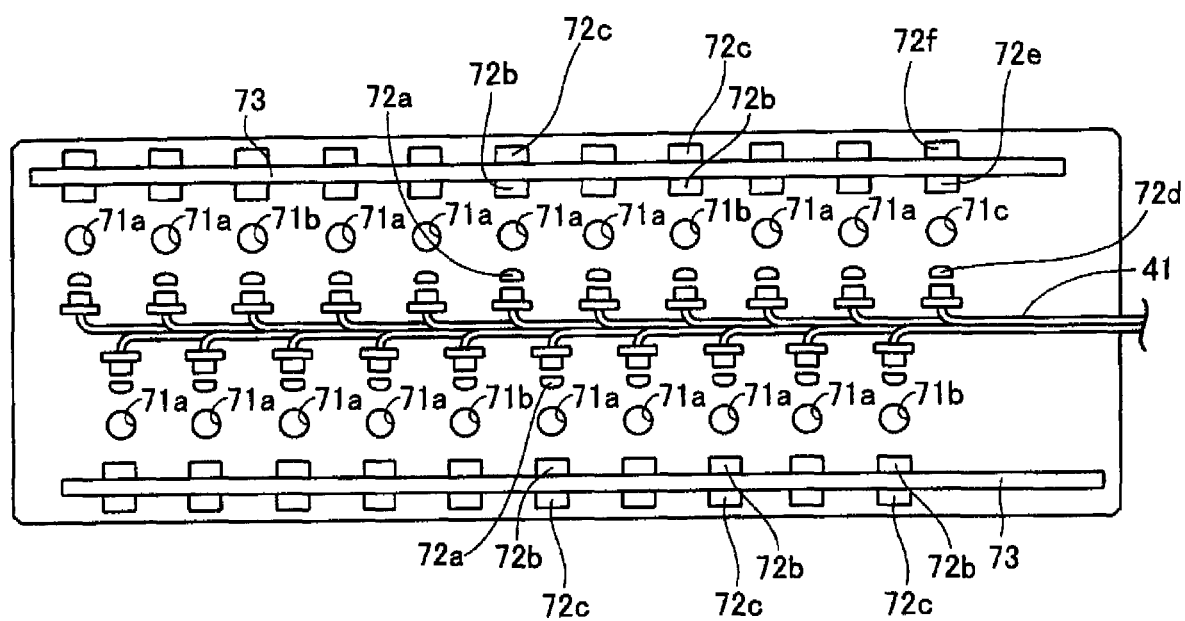
FIG. 4 is a top view of the measuring section of the blood analyzer of FIG. 1.

As shown in FIG. 2, the lamp unit 40 includes a 21-fiber beam splitter optical fiber 41, and has the function of supplying the light used in the optical measurements performed by the measuring section 70. The leading end of the 21-fiber beam splitter optical fiber 41 is connected to the measuring section 70, and conducts the light emitted from the lamp unit 40 to the measuring sample within the cuvettes 250 and 251 placed in the measuring section 70, as shown in FIG. 2. Specifically, the 21-fiber beam splitter optical fiber 41 is arranged so as to supply light from the side surfaces of sixteen insertion holes 71a (described later), four insertion holes 71b, and one reference light measuring hole 71c of the measuring section 70 to the cuvettes 250 and 251, as shown in FIG. 4.

As shown in FIGS. 1 and 2, the reagent dispensing arm 50 is provided to mix the reagent with the blood sample in the cuvette 250 or the cuvette 251 by dispensing a reagent, which is contained in a reagent container (not shown in the drawing) loaded in the rotation device 20, into a cuvette 250 or a cuvette 251 which is also loaded in the rotation device 20. A measurement sample is prepared by adding a reagent to a blood sample. The cuvette transporting section 60 is provided to move the cuvette 250 of the cuvette 251 between the rotation device 20 and the measuring section 70.

The measuring section 70 is provided to receive light over time from the measurement sample which is irradiated by light from the lamp unit 40, and obtain the time course optical information.

The measuring section 70 is configured by a cuvette loader 71, and a sensor 72 which is disposed below the cuvette loader 71, as shown in FIG. 2. The cuvette loader 71 is provided with sixteen insertion holes 71a into which cuvettes 250 or cuvettes 251 are inserted, four insertion holes 71b into which cuvettes 251 are inserted, and a single reference light measuring hole 71c which is used to measure a reference light and into which a cuvette 250 or cuvette 251 is not inserted, as shown in FIG. 4. As shown in FIG. 2, the cuvette loader 71 is provided with a heater 71d to heat, to a predetermined temperature, the cuvettes 250 or a cuvettes 251 which have been inserted into the insertion holes 71a and 71b.

Figure 5:
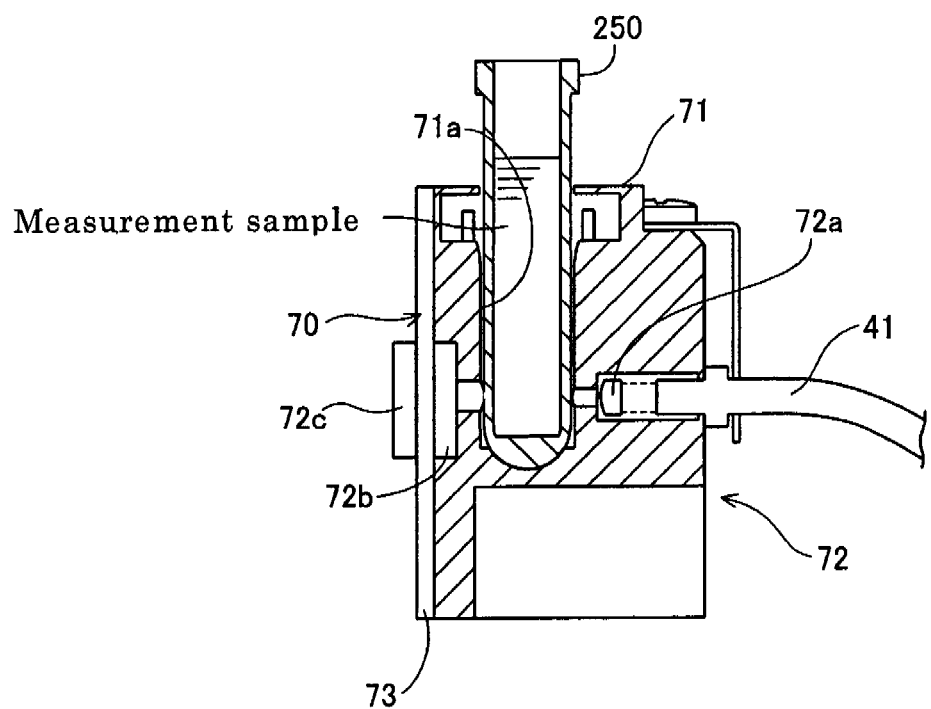
FIG. 5 is a cross section view of the measurement section insertion hole shown in FIG. 4.

As shown in FIG. 5, a cuvette 250 which contains a measurement sample is inserted into the insertion hole 71a or 71b when measurements are performed using the coagulation time method, the synthetic substrate method, and the immunoturbidity method. When measurements are performed using the platelet aggregation method, a cuvette 251 which contains a measurement sample and a mixing element 300 is inserted into an insertion hole 71b, as shown in FIG. 6.

The sensor 72 of the measuring section 70 is configured so as to be capable of optically measuring, under a plurality of conditions, the measurement sample within a cuvette 250 or a cuvette 251 which has been inserted into an insertion hole 71a or 71b. The sensor 72 is provided with a collimator lens 72a, a photoelectric conversion element 72b, and a preamp 72c which correspond to each insertion hole 71a or 71b into which a cuvette 250 can be inserted, as shown in FIGS. 4 through 6. As shown in FIG. 4, a reference light collimator lens 72d, a reference light photoelectric conversion element 72e, and a reference light preamp 72c are provided for the reference light measuring hole 71c.

Figure 6:
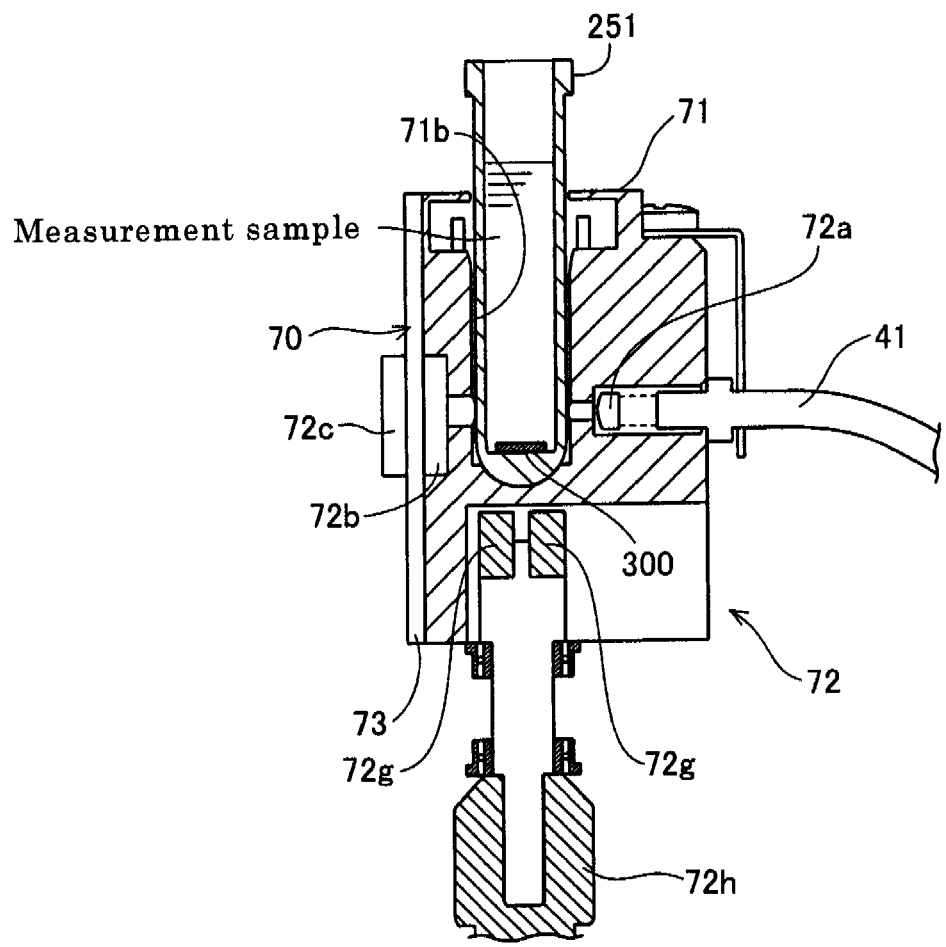
FIG. 6 is a cross section view of the measurement section insertion hole shown in FIG. 4.

As shown in FIG. 6, a rotating member 72g which is configured by a magnet, and a motor 72h which rotates the rotating member 72g are provided in the bottom part of the insertion hole 71b. When measurements are performed using the platelet aggregation method and a cuvette 251 accommodating a mixing element 300 is inserted in an insertion hole 71b, the rotating member 72g is rotated by the drive of the motor 72h. The measurement sample can be mixed during the measurement by rotating the mixing element 300 in conjunction with the rotation of the rotating member 72g. This configuration makes it possible for the blood analyzer 1 of the present embodiment to perform measurements by the platelet aggregation method.

The reference light measuring hole 71c is provided to monitor the characteristics of the light emitted from the beam splitter optical fiber 41. Specifically, the characteristics, such as fluctuation and the like, originating in a halogen lamp (not shown in the drawing) used as the light source of the lamp unit 40, are detected as electrical signals when the light emitted from the bream splitter optical fiber 41 is received by the reference light photoelectric conversion element 72e of a direct sensor 72. The signals corresponding to the transmission light of the measurement sample are corrected by subtracting the characteristics (electrical signals) of the detected light from the signals corresponding to the transmission light of the measurement sample within the cuvette 250 inserted in the insertion hole 71a or 71b. Small differences in light characteristics that may occur in each measurement of the optical information can therefore be suppressed.

As shown in FIGS. 4 and 5, the collimator lens 72a is disposed between the terminus of the beam splitter optical fiber 41, which guides the light emitted from the lamp unit 40 (refer to FIG. 1), and the corresponding insertion hole 71a. The collimator lens 72a is provided to make parallel rays of the light emitted from the beam splitter optical fiber 41. The photoelectric conversion element 72b is mounted on the surface on the insertion hole 71a side of a base plate 73 so as to face the terminus of the beam splitter optical fiber 41, with the insertion hole 71a disposed therebetween. The preamp 72c is mounted on the surface on the opposite side from the insertion hole 71a of the base plate 73. The photoelectric conversion element 72b has the function of detecting the light transmitted through the measurement sample (hereinafter referred to as "transmission light") when light irradiates the measurement sample within a cuvette 250 inserted in the insertion hole 71a, and the function of outputting an electrical signal (analog signal) which corresponds to the detected transmission light. The preamp 72c of the sensor 72 is provided to amplify the electrical signals (analog signals) from the photoelectric conversion element 72b.

Figure 7:
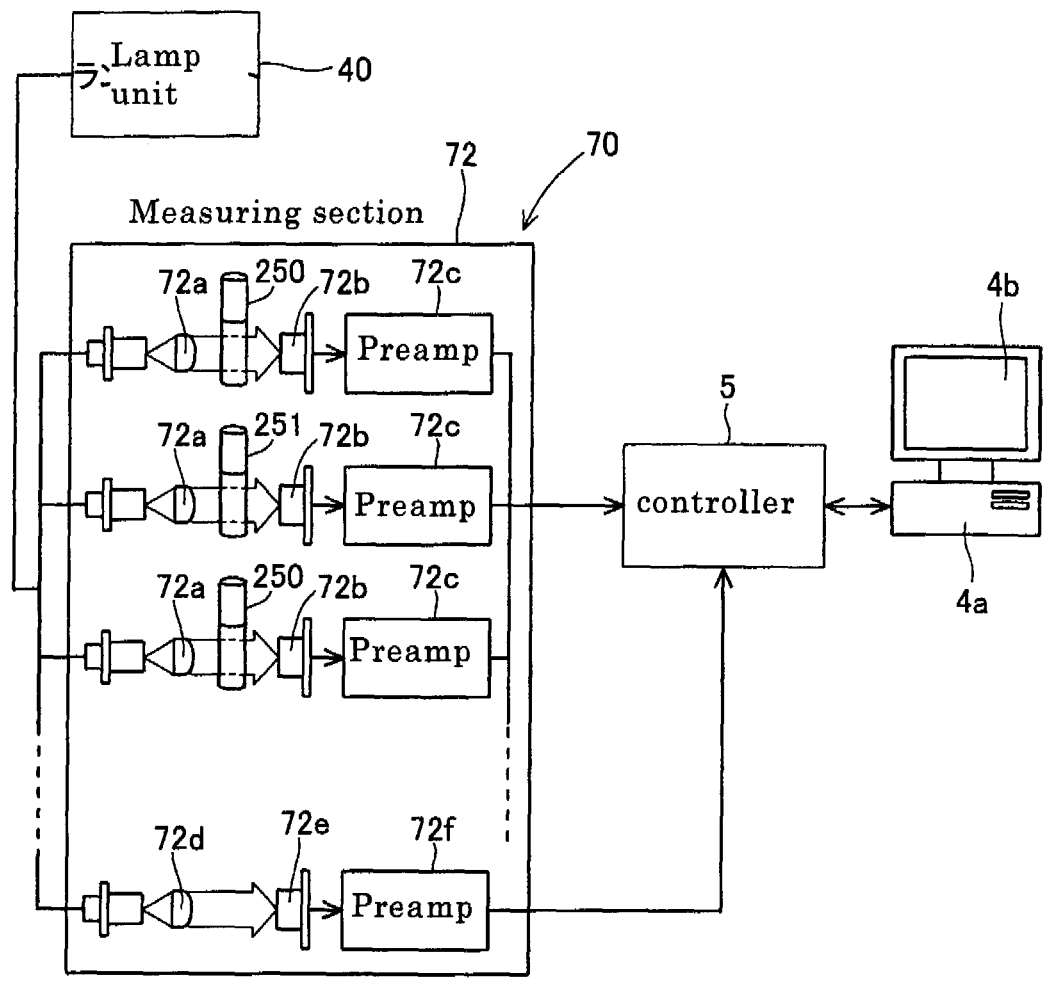
FIG. 7 is a block diagram illustrating the data flow in the measurement operation of the blood analyzer of FIG. 1.

A reference light collimator lens 72d, a reference light photoelectric conversion element 72e, and a reference light preamp 72f provided in the sensor 72, which corresponds to the reference light measuring hole 71c, have the same configuration as the collimator lens 72a, photoelectric conversion element 72b, and the preamp 72c provided in the sensor 72 which corresponds to the insertion hole 71a. As shown in FIG. 7, the reference light photoelectric conversion element 72e is configured to directly receive the light emitted from the beam splitter optical fiber 41 after the light has been transmitted through the reference light collimator lens 72d. That is, the reference light photoelectric conversion element 72e is configured to detect the emitted reference light that does not pass through the cuvette 250 or the cuvette 251 which contains a measurement sample, and output an electrical signal (analog signal) which corresponds to the detected reference light.

The controller 5 is disposed below the measuring section 70. The controller 5 is configured by a CPU, a ROM, a RAM and the like, and has the functions of controlling the operation of the detection device 2 and transporting device 3 and the like, and processing and storing the optical information (electrical signals) output from the measuring section 70, as shown in FIGS. 3 and 7. In the present embodiment, the controller 5 controls the rotation speed and the rotation time of the motor 72h (refer to FIG. 6) of the measuring section 70 during measurements by the platelet aggregation method. Specifically, the controller 5 is capable of controlling the rotation of the motor 72h at a first rotation speed which rotates the mixing element 300 at approximately 400 rpm, and at a second rotation speed which rotates the mixing element 300 at approximately 900 rpm.

The controller 5 has a temperature controller (not shown in the drawing) to control the temperature of the heater 71d (refer to FIG. 2) of the measuring section 70. The temperature controller is configured to control the temperature of the heater 72d of the measuring section 70 in accordance with a set temperature (approximately 37 degrees) input from the control device 4.

The urgent sample receiving section 80 is provided to perform a sample analysis process of a blood sample requiring urgent handling, as shown in FIGS. 1 and 2. The urgent sample receiving section 80 is configured so as to allow an urgent sample to interrupt an on-going sample analysis process of a sample supplied from the transporting device 3. The fluid section 90 is provided to supply a liquid such as a washing liquid to a nozzle provided in each dispensing arm when the shutdown process is executed in the blood analyzer 1.

The control device 4 (refer to FIG. 1) is configured by a personal computer (PC) or the like, and includes a controller 4a configured by a CPU, a ROM, a RAM and the like, a display unit 4b, and a keyboard 4c. The display unit 4b is provided to display the analysis results (change in light absorbance over time, von Willebrand factor activity) obtained by analyzing the digital signal data transmitted from the measuring section 70.

Figure 8:
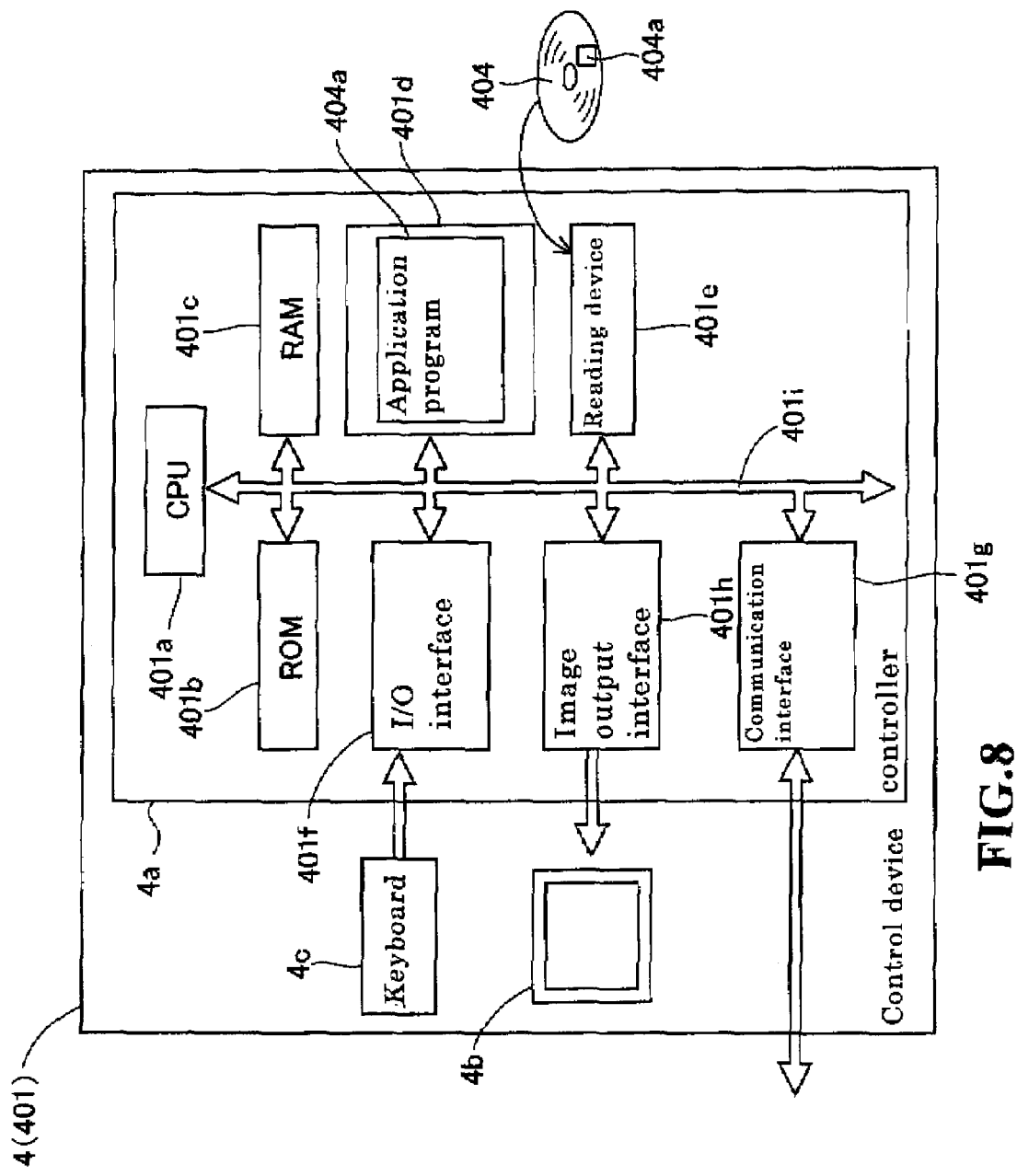
FIG. 8 is a block diagram showing the control device of the blood analyzer of FIG. 1.

The structure of the control device 4 is described below. The control device 4 is a computer 401 mainly configured by the controller 4a, the display unit 4b, and the keyboard 4c, as shown in FIG. 8. The controller 4a is mainly configured by a CPU 401a, ROM 401b, RAM 401c, hard disk 401d, reading device 401e, input/output (I/O) device 401f, communication interface 401g, and image output interface 401h. The CPU 401a, ROM 401b, RAM 401c, hard disk 401d, reading device 401e, I/O interface 401f, communication interface 401g, and image output interface 401h are connected by a bus 401i.

The CPU 401a is capable of executing computer programs stored in the ROM 401b, and computer programs loaded in the RAM 401c. The computer 401 functions as the control device 4 when the CPU 401a executes an application program 404a which is described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is also used as a work area of the CPU 401a when the computer program is being executed.

The hard drive 401d contains various installed computer programs to be executed by the CPU 401a such as an operating system and application program and the like, as well as data used in the execution of these computer programs. Also installed on the hard disk 401d is the application program 404a used for platelet coagulation measurement of the present embodiment.

The reading device 401e is configured by a floppy disk drive, CD-ROM drive, DVD-ROM drive or the like, and is capable of reading the computer programs and data stored on a portable recording medium 404. The portable recording medium 404 stores the platelet aggregation measurement application program 404a, and the application 404a is read from the portable recording medium 404 by the computer 401, which installs the application program 404a on the hard disk 401d.

The application program 404a is not only provided the portable recording medium 404 inasmuch as the application program 404a may also be provided from an external device which is connected to the computer 401 over an electric communication line so as to be capable of communication by this electric communication line (whether wire line or wireless). For example, when the application program 404a is stored on the hard disk of a server computer on the Internet, the computer 401 accesses the server computer and downloads the application program 404a, which is then installed on the hard disk 401d.

An operating system which provides a graphical user interface, such as Windows (registered trademark) or the like, a product of Microsoft Corporation, USA, is installed on the hard disk 401d. The application program 404a of the present embodiment operates on this operating system in the following description.

The I/O interface 401f is configured, for example, by a serial interface such as a USB, IEEE1394, RS232C or the like, a parallel interface such as SCSI, IDE, IEEE1284 or the like, and an analog interface such as a D/A converter, A/D converter or the like. The keyboard 4c is connected to the I/O interface 401f, so that a user can input data in the computer 401 using the keyboard 4c.

The communication interface 401g is, for example, an Ethernet (registered trademark) interface. The computer 401 can send and receive data to and from the controller 5 of the measuring device 2 via the communication interface 401g using a predetermined communication protocol.

The image output interface 401h is connected to the display unit 4b which is configured by an LCD, CRT or the like, so that image signals corresponding to the image data received from the CPU 401a can be output to the display unit 4b. The display unit 4b displays images (screens) in accordance with the input image signals.

The platelet aggregation measurement application program 404a, which is installed on the hard disk 401d of the controller 4a, measures the change in light absorbance over time of the measurement sample using the measurement sample transmission light amount (digital signal data) sent from the controller 5. The von Willebrand factor activity can be obtained based on the maximum change in light absorbance over time.

Figure 9:
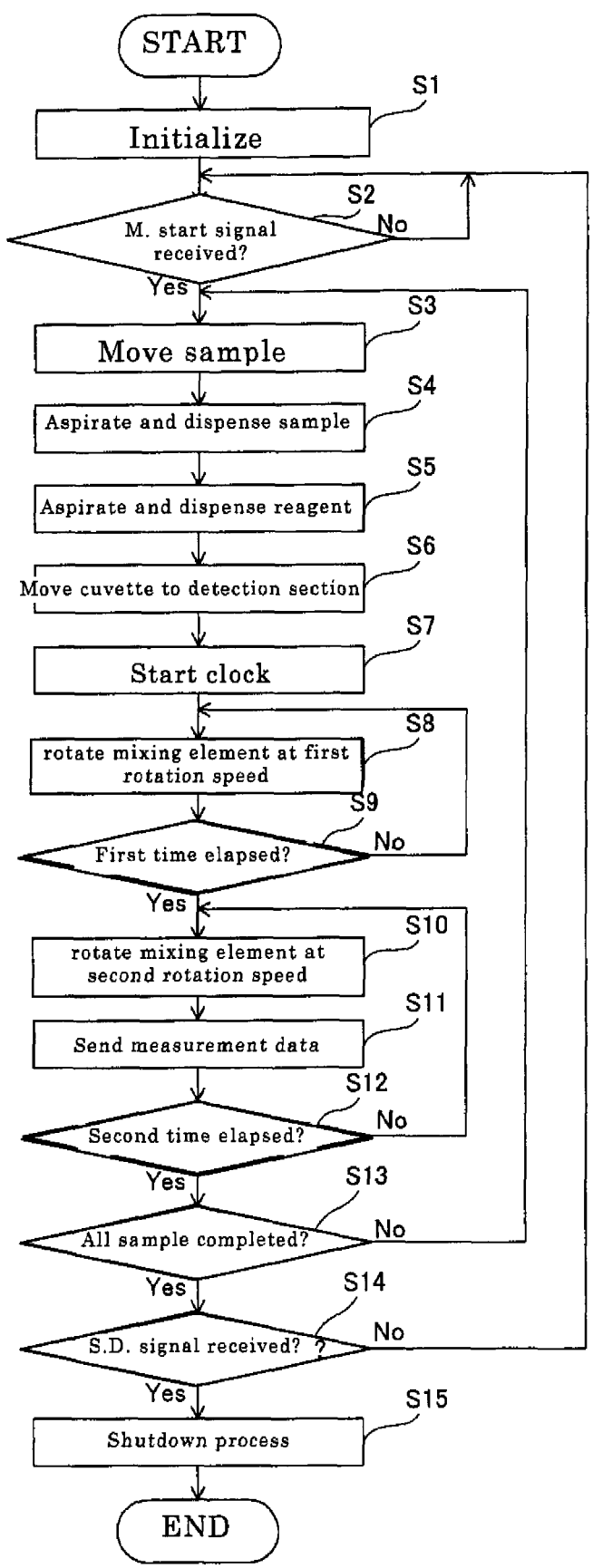
FIG. 9 is a flow chart illustrating the measurement process using the platelet aggregation method of the blood analyzer of FIG. 1.

FIG. 9 is a flow chart illustrating the measurement operation of the platelet aggregation method used by the blood analyzer 1 of the present embodiment. The measurement operation of the platelet aggregation method used by the blood analyzer 1 is described below referring to FIG. 2 and FIGS. 6 through 9. In the following description, the measurement pertains to the von Willebrand ristocetin cofactor (von Willebrand factor activity in blood plasma).

In the measurement operation of the blood analyzer 1, the blood analyzer 1 is first initialized in step S1 of FIG. 9. That is, the control device 4 and the apparatus body are started when the user turns ON the power sources of the control device 4 and the apparatus body (detection device 2 and transporting device 3). When the power sources are turned ON, the software stored in the controller 4a is initialized. In the apparatus body, the programs stored in the controller 5 are initialized. Thereafter, a process is executed to receive sample analysis information input by the user. That is, the user inputs information such as sample numbers and measurement items in a sample analysis list output to the display unit 4b using the keyboard 4c of the control device 4 (refer to FIG. 1). The sample analysis information is then saved in the controller 4. When measurements are performed by the platelet aggregation method, the user places a cuvette 251 which contains a mixing element 300 (refer to FIG. 6) on the cuvette transporting table 23 of the rotation device 20. The user then instructs the control device 4 to start the measurement. A measurement start signal is sent from the controller 4a of the control device 4 to the controller 5 of the apparatus body when the user instructs the control device 4 to start the measurement.

The controller 5 of the apparatus body determines whether or not a measurement start signal has been received in step S2. This determination is repeated when a measurement start signal has not been received. When the measurement start signal is received, the apparatus body (detection device 2 and transporting device 3) starts the analysis process.

In the measurement operation, the transporting device 3 first moves the rack 201, into which the test tube 200 containing the blood samples, has been loaded, to the aspiration position 2a of the detection device 2 in step S3. Then in step S4 the sample dispensing arm 40 aspirates the sample from the test tube, and dispenses the aspirated sample into a cuvette 251 which has been placed on the cuvette transporting table 23. The sample is plasma obtained by centrifuging the blood cells (red blood cells, white blood cells, and platelets) from the blood. The cuvette 251 into which the sample has been dispensed is moved to the heater 71d (refer to FIG. 2) by the cuvette transporting section 60, and is heated to a predetermined temperature by the heater 71d.

In step S5 reagent the reagent dispensing arm 50 aspirates reagent from the reagent table 21 or 22. This reagent contains ristocetin as an activator to immobilize the platelets. At this time the reagent is heated to a predetermined temperature by the pipette part (not shown in the drawing) of the reagent dispensing arm 50 which has a heating function. The cuvette 251 which has been heated by the heater 71d is held by the cuvette transporting section 60, and while in this held state the heated reagent is dispensed into the cuvette 251 by the reagent dispensing arm 50. A measurement sample is thus prepared from a sample and a reagent. At this time the measurement sample containing the sample and the reagent is not in a uniformly mixed condition.

In step S6 the cuvette 251 which contains the measurement sample and the mixing element 300 is moved to the measuring section 70, and inserted into the insertion hole 71b under which are disposed the magnet rotating member 72g and the motor 72h to rotate the rotating member 72g, as shown in FIG. 6.

In step S7 a clock is started for the insertion hole 71b into which the cuvette 251 has been inserted. That is, the time is counted from the insertion of the cuvette 251 into the insertion hole 71b. Light from the beam splitter optical fiber 41 irradiates the measurement sample in the cuvette 251 placed into the insertion hole 71b, and the transmission light passing through the measurement sample is received by the photoelectric conversion element 72b which converts the light to electrical signals.

In step S8 the rotating member 72g is rotated at a predetermined speed by driving the motor 72h. Thus, the mixing element 300 contained in the cuvette 251 is rotated at a first rotation speed (approximately 400 rpm in the present embodiment). The measurement sample composed of the sample and the reagent is agitated so as to be essentially uniformly mixed by the rotation of the mixing element 300. A shear stress which promotes platelet aggregation is not substantially generated at a rotation speed of approximately 400 rpm so that a reaction between the reagent and the sample is not promoted. In step S9 a determination is made as to whether or not a predetermined first time (approximately 15 seconds in the present embodiment) has elapsed since the clock started. The process moves to step S8 when the first time has not elapsed. Thereafter, the measurement sample is mixed by rotating the mixing element 300 at a first speed (approximately 400 rpm) until the first time has elapsed.

When the first time has elapsed, the mixing element 300 is rotated at a second speed (approximately 900 rpm in the present embodiment) in step S10. The measurement sample is strongly mixed and a shearing stress which promotes platelet aggregation is exerted on the platelets in the measurement sample when the mixing element 300 is rotated at approximately 900 rpm. A reaction is promoted between the reagent and the sample by this shearing stress. In step S11 measurement data (light absorbance) are sequentially transmitted in real time from the controller 5 of the apparatus body to the controller 4a of the control device 4 while the mixing element 300 is rotating at the second speed. In step S12 a determination is made as to whether or not a second time (100 seconds in the present embodiment) has elapsed sine the clock started. The process moves to step S10 when the second time has not elapsed. Thereafter, the measurement sample is mixed by rotating the mixing element 300 at the second speed (approximately 900 rpm) and the measurement data (light absorbance) of step S11 are transmitted until the second time has elapsed.

The controller 4a of the control device 4 analyzes the measurement data (light absorbance time series data) received from the controller 5 of the apparatus body. Specifically, the change over time of the maximum absorbance is determined by calculating time differential of the light absorbance time series data. The von Willebrand factor activity is obtained from the change over time of the maximum absorbance. The measurement sample analysis results (in the present embodiment, graph of the change in absorbance, the von Willebrand factor activity and the like) are output to the display unit 4b. The process moves to step S13 when the second time has elapsed in step S12.

A determination is made in step S13 as to whether or not the measurement of all samples has been completed. That is, a determination is made as to whether or not measurements have been completed for all samples specified for measurement by the platelet aggregation method based on the sample analysis information input by the user in step S2. When measurement of all sample has not been completed, the process returns to step S3 and the measurement process of steps S3 through S12 are performed. When measurement of all samples has been completed, the process advances to step S14.

After measurements have ended, the user issues a device shutdown instruction for the control device 4. When the user issues a shutdown instruction, a shutdown signal is sent to the controller 4a of the control device 4. The controller 4a of the control device 4 determines whether or not a shutdown signal has been received from the user in step S14. When a shutdown signal has not been received, the process moves to step S2 and the processes of steps S2 through S13 are performed.

When the shutdown signal has been received, the shutdown process is executed in step S15. The shutdown process automatically turns OFF the power supply of the blood analyzer 1 to end the operation of the blood analyzer 1.

Figure 10:
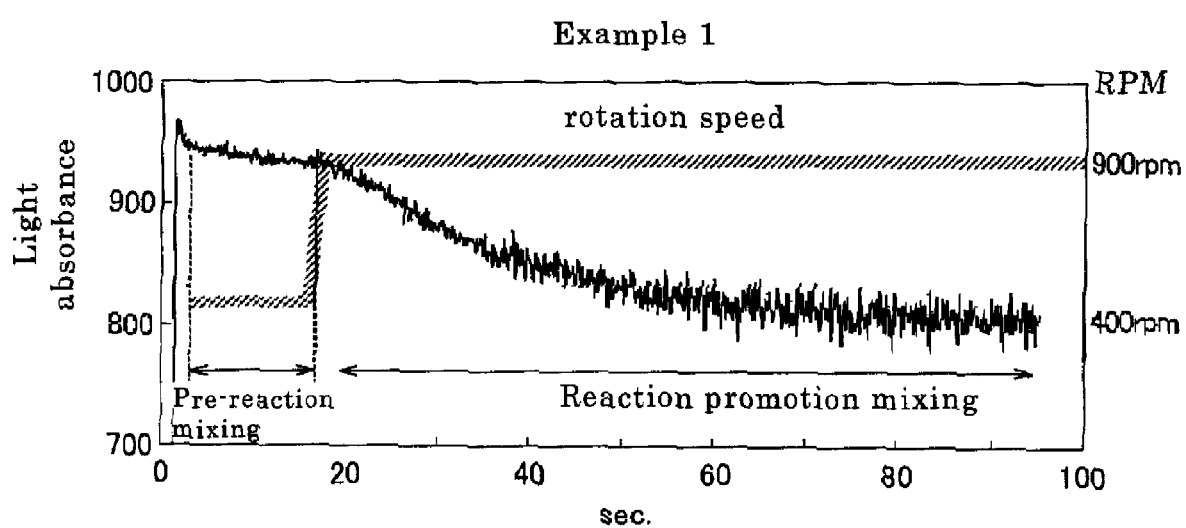
FIG. 10 is a graph showing the change in the degree of light absorbance when measurement is performed in two-stage mixing.
Figure 11:
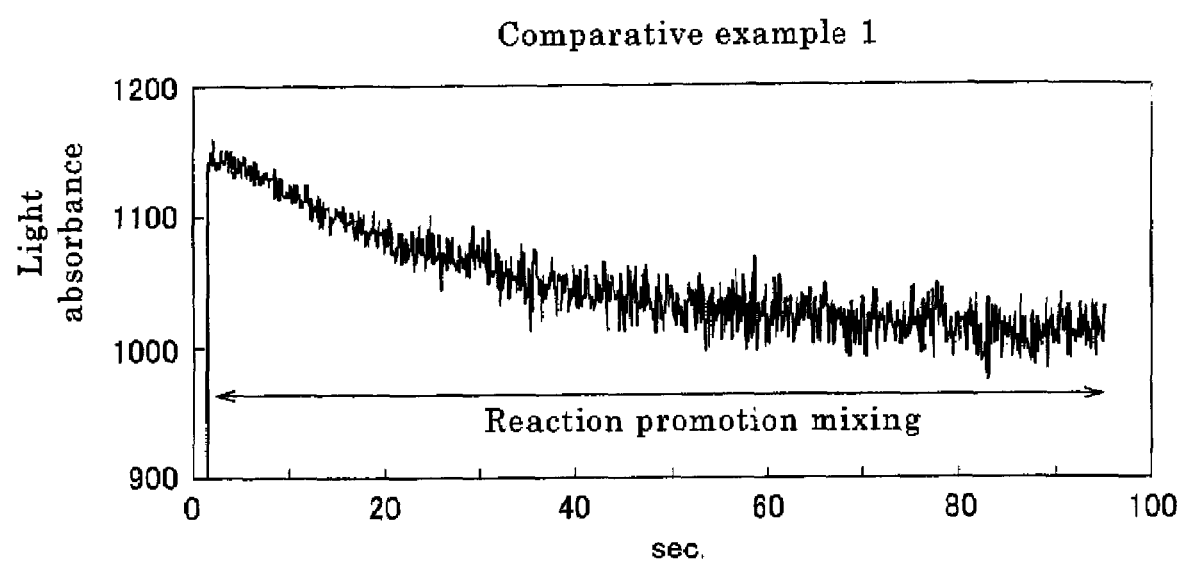
FIG. 11 is a graph showing the change in the degree of light absorbance when measurement is performed in single stage mixing.

The effectiveness of the two-stage mixing operation is described below. FIG. 10 is a graph showing the measurement results of light absorbance measured by mixing to make the measurement sample uniform (hereinafter "pre-reaction mixing"), and mixing to promote a reaction between the sample and the reagent (hereinafter "reaction promotion mixing") in the blood analyzer 1 of the present embodiment. FIG. 11 is a graph showing the measurement results of light absorbance measured by single-stage mixing using only the reaction promotion mixing in the blood analyzer 1 of the present embodiment.

FIG. 10 shows the change over time of light absorbance when the pre-reaction mixing is performed for approximately 15 seconds at a mixing element rotation speed of approximately 400 rpm, and thereafter the reaction promotion mixing is performed at a rotating element rotation speed of approximately 900 rpm (example 1). In example 1, light absorbance decreases smoothly during the seconds of pre-reaction mixing, and there is thought to be essentially no platelet aggregation occurring. The sample and reagent are also rendered substantially uniform in the 15 seconds of pre-reaction mixing. There is a large change over time of light absorbance after the reaction promotion mixing starts, and a reaction between the sample and the reagent is thought to be promoted.

FIG. 11 shows the change over time of the light absorbance in the case of single stage mixing from the beginning at a mixing element rotation speed of approximately 900 rpm (that is, a rotation speed of approximately 900 rpm during both pre-reaction mixing and reaction promotion mixing) (comparative example 1). In comparative example 1, the change over time (slope) of the light absorbance increases from the start and it is thought that a platelet aggregation reaction occurs because the sample and reagent are not rendered uniform, as shown in FIG. 11.

Comparative examples determining the rotation speed of the mixing element during pre-reaction mixing are described below. The comparative examples are described in terms of measuring vWF (von Willebrand factor) ristocetin cofactor activity. The measurement samples used in these measurements are prepared using sample from plasma which contains vWF factor removed from blood cells, and reagent which contains immobilized platelets and ristocetin. The change in light absorbance is monitored photometric measurement while mixing the measurement sample. The vWF activity (%) is calculated based on the change in light absorbance. The vWF activity is designated a normal value when the value is 50 to 150% of a standard value, designated a low value when less than 50%, and designated a high value when greater than 150%.

The test conditions of the comparative examples include the cuvette and mixing element have the same size and shape as in the previously described embodiment, and the amounts of the sample, dilution liquid, and reagent are 10 µl, 30 µl, and 150 µl, respectively.

In the comparative examples; samples of known activity (activity of 0%, 8.7%, and 17.4%) were measured when the rotation speed of the mixing element during pre-reaction mixing is approximately 900 rpm (comparative example 1), approximately 400 rpm (example 1), and approximately 150 rpm (example 2), and the results are plotted in the graphs shown in FIGS. 10 and 11. The maximum slope (maximum light absorbance change rate) in the graph was calculated from the respective graphs of the measurement results using a predetermined algorithm. The process was conducted several times and the average value of the determined slope (light absorbance change rate) was calculated. The calculated results are shown in Table 1 below.

TABLE 1

| Pre-reaction mixing speed | vWF (%) | | | Sensitivity (absorbance change rate) |
| --- | --- | --- | --- | --- |
| | 0 | 8.7 | 17.4 | 17.4-0% |
| 900 rpm | 0.043 | 0.037 | 0.045 | 0.002 |
| 400 rpm | 0.007 | 0.016 | 0.031 | 0.024 |
| 150 rpm | 0.009 | 0.013 | 0.021 | 0.012 |

As shown in Table 1, the measured values (absorbance change rate) when the activity was 0%, 8.7%, and 17.4% and the rotation speed of the mixing element was approximately 900 rpm during pre-reaction mixing were 0.043, 0.037, and 0.045, respectively. The measured values when the activity was 0%, 8.7%, and 17.4% and the rotation speed of the mixing element was approximately 400 rpm during pre-reaction mixing were 0.007, 0.016, and 0.031, respectively. The measured values when the activity was 0%, 8.7%, and 17.4% and the rotation speed of the mixing element was approximately 150 rpm during pre-reaction mixing were 0.009, 0.013, and 0.021, respectively. These values are plotted on the horizontal axis and the vertical axis as the activity and light absorbance change rate on a broken line graph shown in FIG. 12.

Figure 12:
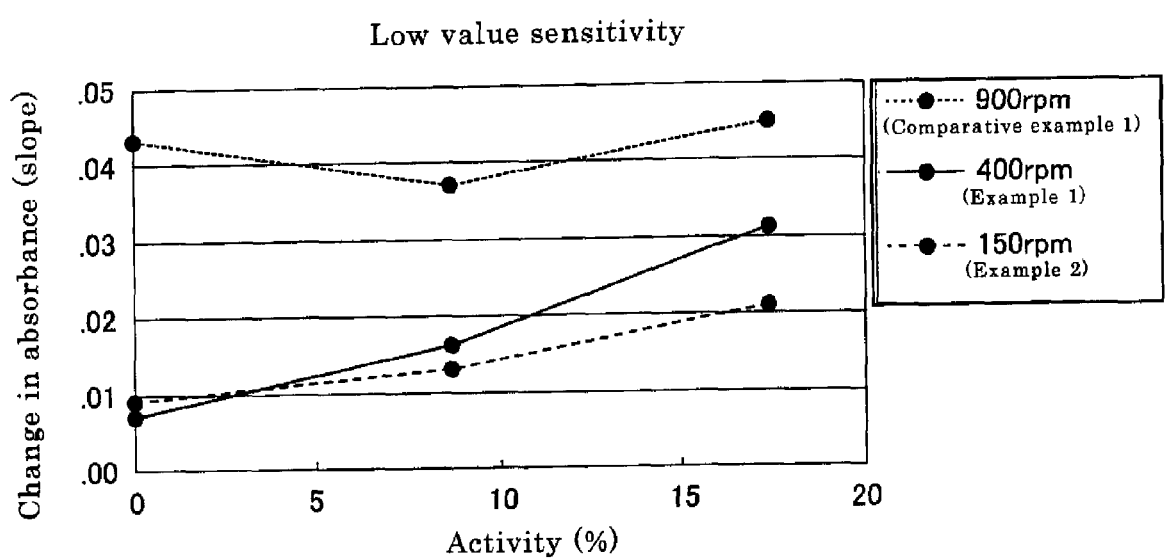
FIG. 12 is a line graph showing the measurement results of comparative experiments in which the rotation speed is changed in mixing prior to the reaction.

As can be understood from FIG. 12, the measurement results were unstable in comparative example 1 in which only reaction promotion mixing was performed because the light absorbance change rate did not exhibit a monotonic increase relative to the activity. The reasons for this are considered below. In the comparative example, local reaction proceed because the reaction starts while the reagent and the sample of the measurement sample are in a non-uniform state. The reaction proceeds locally when the mixing starts since there is little activated vWF in the sample when the activity has a particularly low value, and there is a marked difference in the amount of reaction between a localized reaction of activated vWF and a reaction with scant reaction progress. Therefore, the shape (change over time of the absorbance) of the graph shown in FIG. 11 fluctuates at each measurement even when the same sample is measured several times, so that the measurement results which represent the degree of vWF activity calculated from the graph shape are unstable.

The measurement results were stable in the first and second examples which used two-stage mixing that included pre-reaction mixing and reaction promotion mixing because the light absorbance change rate did exhibit a monotonic increase relative to the activity. The reasons for this are considered below. In the first and second examples, the reagent and the sample are thought to have been rendered essentially uniform at the start of the reaction promotion mixing due to the pre-reaction mixing during which there was essentially no reaction induced between the reagent and the sample before the reaction promotion mixing. Therefore, a reaction corresponding to the amount of activity occurred since the reaction had completely progressed even though the vWF activity in the sample was low. For this reason the measurement results calculated from the graph shape are thought to be stable since there was little fluctuation of the graph shape between measurements in FIG. 12 even when the same sample was measured several times.

In the experimental results above, the difference between the measured value at 0% activity, and the measured value at 17.4% activity was calculated for the comparative example 1, and the first and second examples in order to evaluate the measurement sensitivity in the comparative example 1, and the first and second examples. The calculated results are shown in Table 1. The calculated results of the comparative example 1, and the first and second examples are 0.002, 0.024, and 0.012, respectively. It is clear from these results that the sensitivity is higher in the first and second examples in which two-stage mixing that included pre-reaction mixing and reaction promotion mixing was performed compared to the comparative example 1 in which only the reaction promotion mixing was performed. It is further clear that example 1 in which pre-reaction mixing was performed at approximately 400 rpm has higher sensitivity than the example 2 in which pre-reaction mixing was performed at 150 rpm.

Experiments determining the mixing time of the pre-reaction mixing are described below. The mixing time must be optimized because the reagent and sample are rendered insufficiently uniform when the pre-reaction mixing time is short when measuring a high value vWF sample, and the reaction between the reagent and the sample progressed gradually when the pre-reaction mixing time was long. This experiment was conducted as follows. Samples of known high activity (activity of 178%) and samples of normal value (vWF 89%) were measured when the mixing time during pre-reaction mixing were measured by changing the mixing time of the pre-reaction mixing (5, 10, 15, 20, and 40 seconds) with a pre-reaction mixing speed of approximately 400 rpm which exhibited an optimum low sensitivity. Each measurement was performed ten times and the average value of the measurement results was calculated. The difference was calculated between the measurement results of high value samples and the measurement results of low value samples to verify the sensitivity of the measurement of high value samples. These measurement results are shown in Table 2 below.

TABLE 2

| vWF (%) | Mixing time (seconds) | | | | |
|---|---|---|---|---|---|
| | 5 | 10 | 15 | 20 | 40 |
| 178% | 0.417 | 0.453 | 0.459 | 0.435 | 0.282 |
| 89% | 0.135 | 0.229 | 0.262 | 0.285 | 0.284 |
| 178 − 89% | 0.282 | 0.224 | 0.197 | 0.15 | −0.002 |

Figure 13:
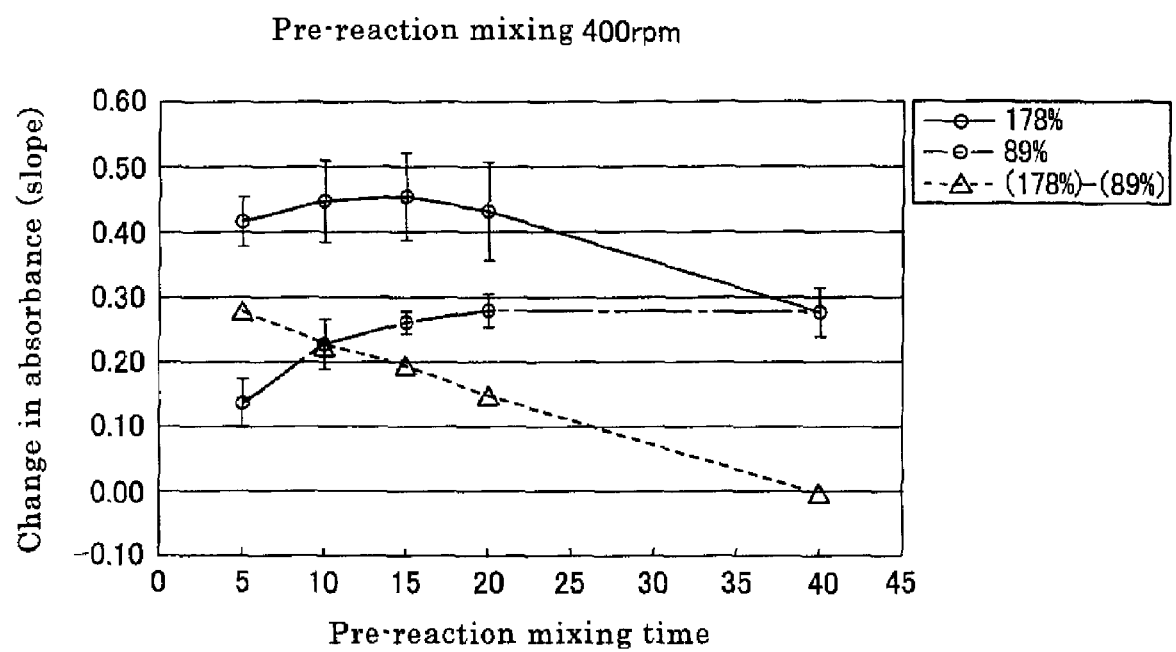
FIG. 13 is a broken line graph showing the measurement results of comparative experiments in which the mixing time is changed in mixing prior to the reaction.

As shown in Table 2, the high value sample measurement results (average value of ten measurements) were 0.417, 0.453, 0.459, 0.435, and 0.282 when the pre-reacting mixing time was 5, 10, 15, 20, and 40 seconds, respectively. The normal value measurement results (average value of ten measurements) were 0.135, 0.229, 0.262, 0.285, and 0.284 when the pre-reaction mixing time was 5, 10, 15, 20, and 40 seconds, respectively. The difference between the high value and normal value measurement results was 0.282, 0.224, 0.197, 0.150, and −0.002 when the pre-reaction mixing time was 5, 10, 15, 20, and 40 seconds, respectively. The measurement results are plotted on the broken line graph shown in FIG. 12 with the pre-reaction mixing time and absorbance change rate plotted on the horizontal axis and vertical axis, respectively. FIG. 13 shows the range of the ten measurement results.

As shown in Table 2 and FIG. 13, the difference between the high value and low value measurement results exhibited a monotonic decrease as the pre-reaction mixing time increased. That is, the high value sensitivity increased as the mixing time decreased. The normal value measurement results show relatively slight reaction when the mixing time was 5 and 10 seconds, and relatively great reaction when the mixing time was 15 to 40 seconds. From these results it is thought that a pre-reaction mixing time of 15 or 20 seconds is suitable to produce sufficient reaction in normal value sample.

The reproducibility of the measurement results was verified based on the measurement results of the normal value samples. That is, the average value, standard deviation, and fluctuation coefficient were calculated from the ten measurement results using normal value (89%) samples and a mixing time of 5 to 40 seconds. The calculated results are shown in Table 3 below.

TABLE 3

| vWF | Mixing time (seconds | | | | |
|---|---|---|---|---|---|
| 89% | 5 | 10 | 15 | 20 | 40 |
| Average | 0.135 | 0.228 | 0.261 | 0.284 | 0.284 |
| S.D. | 0.019 | 0.020 | 0.010 | 0.011 | 0.023 |
| Fluctuation coefficient (%) | 14% | 9% | 4% | 4% | 8% |

As shown in Table 3, the standard deviation was 0.019, 0.020, 0.010, 0.011, and 0.023 at pre-reaction mixing times of 5, 10, 15, 20, and 40 seconds, respectively. The fluctuation coefficients were 14%, 9%, 4%, 4%, and 8% at pre-reaction mixing times of 5, 10, 15, 20, and 40 seconds, respectively. From the perspective of reproducibility therefore, it is thought that a pre-reaction mixing time of 15 seconds is optimum since the minimum values of the standard deviation and fluctuation coefficient, which represent the least data dispersion, occur when the pre-reaction mixing time is 15 seconds.

In the embodiment and examples described above, stable measurement results were obtained by obtaining optical information from measurement samples while the measurement sample was mixed at a rotation speed of approximately 900 rpm after the measurement sample had been mixed at a rotation speed of approximately 400 rpm under the experimental conditions (cuvette and mixing element size and shape, amounts of reagent and sample and the like) described previously.

The embodiment and examples of the present disclosure are examples in all aspects and are not to be construed as limiting. The scope of the present invention is represented in the scope of the claims and not in the description of the embodiment and examples, and may be variously modified insofar as such modifications remain within the scope and meaning and equivalences of the claims.

For example, although the embodiment and examples have been described by way of examples of measuring von Willebrand factor ristocetin cofactor using von Willebrand reagent which contains ristocetin and immobilized platelets as a reagent and using plasma as a sample, the present invention is not limited to this arrangement inasmuch as platelet aggregation may also be measured using plasma which contains platelets as a sample, and using reagent which contains collagen, ADP (adenosine diphosphate), epinephrine, or arachidonic acid as the reagent.

Although the embodiment and examples have been described by way of example using a pre-reaction mixing time of 15 seconds and a pre-reaction mixing speed of 400 rpm, the present invention is not limited to this arrangement inasmuch as these values are values pertaining to the specific measurement conditions (measurement item, cuvette and mixing element shape and size, amounts of reagent and sample and the like) described in the embodiment and examples, and the mixing time and rotation speed appropriate for other experimental conditions must be determined for those conditions.

Although the embodiment and examples have been described in terms of mixing a measurement sample by rotating a mixing element 300, the present invention is not limited to this arrangement inasmuch as mixing may be accomplished by vibrating or oscillating the cuvette to effect mixing, mixing may be accomplished by ultrasound, and mixing may be accomplished by pipetting. These mixing methods may also be accomplished by two-stage mixing including a pre-reaction mixing and a reaction promotion mixing to obtain the effect of the present invention.

Although a user places a cuvette 251 which already contains a mixing element 300 in the example of the embodiment, the present invention is not limited to this arrangement inasmuch as a device may also be provided to automatically supply a mixing element to a cuvette which is also supplied automatically.

Although platelet aggregation is evaluated by detecting transmission light in the above embodiment and examples, the present invention is not limited to this arrangement inasmuch as platelet aggregation may also be evaluated by scattered light.

Although two-stage mixing which include pre-reaction mixing and reaction promotion mixing has been described in the examples of the embodiment and examples, the present invention is not limited to this arrangement inasmuch as the reaction promotion mixing may be divided into two stages so as to accomplish mixing in three stages.

Although pre-reaction mixing is accomplished as a constant speed (approximately 400 rpm) in the examples of the embodiment and examples, the present invention is not limited to this arrangement since the mixing speed need not be constant insofar as the speed is such as does not produce a reaction (aggregation) between the sample and the reagent.

What is claimed is:

1. A platelet aggregation measuring method comprising:
    preparing a measurement sample by dispensing into a container a sample and a reagent which includes a platelet activator;
    mixing the measurement sample in the container by rotating a mixing element in the container for a predetermined time needed to substantially uniformly mix the sample and the reagent at a first speed which essentially does not produce platelet aggregation;
    mixing the measurement sample in the container by rotating the mixing element in the container at a second speed which promotes platelet aggregation and is greater than the first speed after mixing the sample at the first speed;
    obtaining optical information from the measurement sample by irradiating the measurement sample in the container and receiving light over time from the measurement sample while mixing the measurement sample at the second speed; and
    analyzing aggregation of platelets in the sample based on the optical information.

2. The platelet aggregation measuring method of claim 1, wherein
    the platelet activator comprises at least one selected from the group consisting of ristocetin, collagen, ADP, epinephrine, and arachidonic acid.

3. The platelet aggregation measuring method of claim 1, further comprising a step of providing a container which contains the mixing element,
    wherein:
    the mixing element comprises a magnet or a magnetic material;
    the step of mixing the measurement sample at the first speed comprises a step of mixing the measurement sample by rotating the mixing element at the first speed by rotating a rotating member which comprises a magnet or a magnetic material provided in the outer part of the container; and
    the step of mixing the measurement sample at the second speed comprises a step of mixing the measurement sample by rotating the mixing element at the second speed by rotating the rotating member.

4. The platelet aggregation measuring method of claim 1, wherein the second speed is double or more than double the first speed.

5. The platelet aggregation measuring method of claim 1, wherein the step of mixing the measurement sample at the first speed, and the step of mixing the measurement sample at the second speed are executed continuously.

6. The platelet aggregation measuring method of claim 1, wherein the time during which the step of mixing the measurement sample at the second speed is executed is longer than the time during which the step of mixing the measurement sample at the first speed is executed.

7. The platelet aggregation measuring method of claim 1, wherein the step of analyzing the platelet aggregation comprises a step of obtaining a von Willebrand factor activity.

8. The platelet aggregation measuring method of claim 1, wherein the first speed is a speed which essentially does not generate shear stress on platelets in the measurement sample, and the second speed is a speed which generates shear stress on platelets in the measurement.

9. The platelet aggregation measuring method of claim 1, wherein each step comprising the method is conducted automatically on a blood analyzer.

10. A platelet aggregation measuring method comprising:
    preparing a measurement sample by dispensing into a container a sample and a reagent which includes a platelet activator;
    mixing the measurement sample in the container by rotating a mixing element in the container for a predetermined time needed to substantially uniformly mix the sample and the reagent at a first speed which essentially does not generate shear stress on platelets in the measurement sample;
    mixing the measurement sample in the container by rotating the mixing element in the container at a second speed which generates shear stress on platelets in the measurement and is greater than the first speed after mixing the sample at the first speed;
    obtaining optical information from the measurement sample by irradiating the measurement sample in the container and receiving light over time form the measurement sample while mixing the measurement sample at the second speed; and
    analyzing aggregation of platelets in the sample based on the optical information.

* * * * *